United States Patent [19]

Hüllstrung et al.

[11] 4,287,350

[45] Sep. 1, 1981

[54] PROCESS FOR THE PREPARATION OF THIAZOLIDINE-2-THIONES

[75] Inventors: Dieter Hüllstrung, Leverkusen; Jürgen Trimbach, Cologne, both of Fed. Rep. of Germany

[73] Assignee: Bayer Aktiengesellschaft, Fed. Rep. of Germany

[21] Appl. No.: 131,807

[22] Filed: Mar. 19, 1980

[30] Foreign Application Priority Data

Mar. 24, 1979 [DE] Fed. Rep. of Germany ....... 2911661

[51] Int. Cl.$^3$ ............................................. C07D 277/04
[52] U.S. Cl. ................................... 548/182; 548/183; 548/189; 548/186
[58] Field of Search ................ 548/189, 183, 186, 182

[56] References Cited

U.S. PATENT DOCUMENTS 3,215,703  11/1965  Sullivan et al. ...................... 548/182
3,215,704  11/1965  Kinstler .............................. 548/182
3,370,051   2/1968  Sullivan et al. ...................... 548/182

*Primary Examiner*—Nicholas S. Rizzo
*Attorney, Agent, or Firm*—Connolly and Hutz

[57] ABSTRACT

A process for the production of thiazolidine-2-thiones by the reaction of 1 mol of an amino ethanol with from 2 to 2.1 mol of carbon disulphide at from 20° to 200° C. and from 0.1 to 5 bar pressure, characterized in that the liquid phase is introduced continuously into the first intimate contact with the gaseous phase containing carbon disulphide in a continuous single stage process in at least two consecutive reaction zones, wherein the liquid phase in introduced continuously into the first reaction zone, conveyed toward the last reaction zone and removed downstream of the last reaction zone and wherein the gaseous phase is introduced continuously into the last reaction zone, conveyed toward the first reaction zone and removed downstream of the first reaction zone. The product obtained can be used as a vulcanization accelerator for rubber.

8 Claims, No Drawings

PROCESS FOR THE PREPARATION OF THIAZOLIDINE-2-THIONES

This invention relates to a process for the preparation of thiazolidine-2-thiones by the reaction of amino alcohols with carbon disulphide.

It is known from J. Chem. Soc. 1949, 789 to prepare N-substituted thiazolidine-2-thiones by reacting the corresponding N-substituted amino ethanols and carbon disulphide in an autoclave at from 120° to 140° C. for from 2 to 5 hours in a single stage pressure reaction. The yield is from 65 to 75%. U.S. Pat. No. 3,215,703 states that these products have to be recrystallized before they may be used as vulcanisation accelerators for rubbers owing to the large quantities of coloured and foul-smelling by-products. An improved process according to U.S. Pat. No. 3,215,704 is carried out at a temperature of from 75° to 160° C. for about 6 hours in a two stage reaction under atmospheric pressure in a stirrer-type boiler equipped with a reflux condenser. The yield is substantially higher. However, the commercial exploitation of this process is accompanied by problems and risks inter alia, because of the evolution of waste gases containing carbon disulphide toward the end of the batchwise running reaction which necessitates careful monitoring of the individual stages of the reaction. In addition, the process is also unsatisfactory owing to the long reaction time of 6 hours.

It has accordingly been found that thiazolidine-2-thiones may be prepared in an excellent yield at a pressure of from 0.1 to 5 bar and at a temperature of from 20° to 200° C. from the reaction of 1 mol of the corresponding amino ethanol and from 2 to 2.1 mol of carbon disulphide wherein the liquid phase containing the amino ethanol is brought into intimate contact with the gaseous phase containing carbon disulphide in a single stage process in at least two consecutive reaction zones, the liquid phase being introduced into the first reaction zone, passed toward the last zone and removed downstream of the last zone, while the gaseous phase is simultaneously introduced into the last reaction zone, passed toward the first zone and removed downstream of the first zone.

The process is intended to be operated continuously.

Compounds corresponding to the general formulae (1) and (2) below are mentioned as examples of thiazolidine-2-thiones which may be prefered according to the present invention:

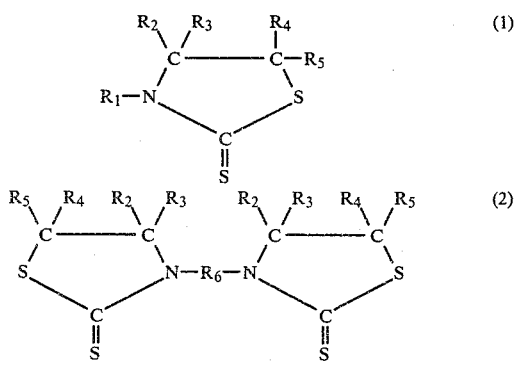

wherein $R_1$ represents hydrogen, a straight, branched or cyclic alkyl or alkenyl radical which may be interrupted by N, O or S and which may be substituted one or more times by aryl, hydroxyl and/or halogen;

$R_2$ to $R_5$, which may be the same or different, each represents hydrogen, phenyl or alkyl or $R_2$ and $R_4$ or $R_3$ and $R_5$ together with the carbon atoms to which they are attached complete a polymethylene bridge having from 2 to 6 carbon atoms, and $R_6$ represents an alkylene, cycloalkylene or xylylene group.

The substituent $R_1$ preferably represents $C_1$–$C_{18}$ alkyl, in particular $C_1$–$C_8$ alkyl, $C_3$–$C_{18}$ alkenyl, in particular $C_3$–$C_8$ alkenyl, which may be substituted by a $C_6$–$C_{12}$ aryl group, a hydroxy group or by a halogen, such as chlorine, bromine, iodide or fluorine.

In the substituents $R_2$ to $R_5$, alkyl is preferably $C_1$–$C_{18}$ alkyl, in particular $C_1$–$C_8$ alkyl. This alkyl group may optionally be substituted by one or more, preferably one, halogen (chlorine, bromine, iodine or fluorine), OH-group, COOH-group or COOR$_7$-group wherein $R_7$ represents $C_1$–$C_5$ alkyl.

The substituent $R_6$ preferably represents $C_2$–$C_6$ alkylene, $C_5$ or $C_6$ cycloalkylene or a xylylene group.

The amino alcohols used as starting materials are preferably compounds corresponding to the following general formula (3) and (4):

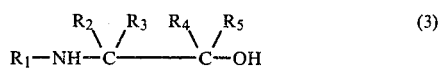

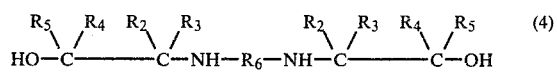

wherein $R_1$ to $R_6$ are as defined above.

The term "reaction zones" is used above in the sense of containers which are joined together, for example, by pipes, chutes, slots, sieve plates or perforated plates, if they enable the requirement for intimate contact between the gaseous phase the liquid phase to be met for example, boilers equipped with feed pipes and delivery pipes for the gaseous and liquid phase, boilers of this type provided with stirrers, levels of bubble trays, perforated plates, nozzle mixers designed in the manner of distillation columns or portions of a packed column provided with packing material which are designated as "tray" or "level" by the skilled man without a recognisable upper and lower limit. Various types of reaction zone may obviously be combined to form the apparatus in which the process according to the present invention is carried out, for example stirrer-type boilers and portions of packed columns or levels of bubble trays and portions of packed columns.

Generally speaking, the reaction zones are neither heated nor cooled. The individual reaction zones may, however, be provided with heat exchange units in order to dissipate the heat produced by the reaction or to supply heat. According to a preferred embodiment of the present process, however, some of the heat produced by the reaction is removed by evaporation of the amino ethanol present in the reaction zones or of the thiazolidine-2-thiones formed, wherein, for example, the gas stream is cooled upstream or downstream of the first reaction zone and the liquid condensed in this process is recirculated into one of the reaction zones. The waste gas mixture obtained in this way is virtually free from carbon disulphide.

Similarly some of the reaction heat is preferably dissipated by cooling the liquid phase upstream or downstream of the last reaction zone.

The liquid mixture produced downstream of the last reaction zone contains, in addition to the desired thiazolidine-2-thiones, some carbon disulphide and dissolved by-products. The carbon disulphide may be removed from the mixture in a known manner by introducing, for example, nitrogen or water vapour. According to a preferred embodiment, however, it is reacted completely by the addition of a quantity of the amino ethanol corresponding to at least twice the molar quantity of the free carbon disulphide still present, to form a dissolved by-product.

The by-product may remain in the thiazolidine-2-thione produced according to the present invention, particularly if it is only present in small quantities. According to a preferred embodiment, however, it is separated from the thiazolidine-2-thione and recirculated into at least one of the reaction zones. The separation of the by-product is effected, for example, by distillation.

According to another preferred embodiment, the by-product is mixed, after the separation of the thiazolidine-2-thione, with the amino ethanol being introduced to the first reaction zone.

It is surprising that the measures according to the present invention allow thiazolidine-2-thiones to be prepared in a virtually quantitative yield, based on the amino ethanol used, as well as the carbon disulphide, in a continuous process in which the waste gas stream is virtually free from carbon disulphide. It is also surprising that the products may even be obtained in a good yield using a total residence time of the liquid phase in the reaction zones of from 10 to 120 minutes, preferably from 10 to 60 minutes.

The thiazolidine-2-thiones produced according to the present invention, which occur in liquid form here may, if they are solid at room temperature, be converted into the conventional commercial solid state in a known manner by cooling, for example on a doctor roller, without further purification.

The present invention is illustrated below by way of the following Examples in which all parts and percentages are to be considered as parts, by weight, and percentages, by weight.

EXAMPLE 1

The reaction apparatus which is insulated from thermal irradiation consists of a 1 l three-necked flask on whose central neck is placed a column packed with glass Raschig rings. A reflux condenser charged with cooling water is placed thereon. A feed pipe A which is connected via a metering pump to the reservoir A for the feed mixture is located between the column and condenser. A feed pipe B projects through the second neck of the flask to the bottom of the flask which is connected via an additional metering pump to the carbon disulphide reservoir B. The outflow is removed through the third ground section of the flask in such a way that the flask constantly remains about 65% full. 800 g/h of liquid containing 407 g/h of N-methylaminoethanol are continuously pumped through feed pipe A, while the remaining quantity originates from the recirculation. 842 g/h of carbon disulphide are pumped in continuously through feed pipe B. 1131 g/h of reaction mixture, the temperature of which is 161° C., are removed continuously from the flask. The mixture is blown through with nitrogen under cooling and 17 g/h of carbon disulphide are condensed from the waste gas with the aid of a cold trap at −75° C. and are recirculated into the reservoir B. 720 g/h of N-methyl-thiazolidine-2-thione having a melting point of from 68° to 70° C. are obtained from the remaining reaction mixture by vacuum distillation at 130° C. The sump product, 394 g/h, is recirculated to the reservoir A.

A gas mixture which is at 25° C. and contains, in addition to hydrogen sulphide and carbon oxysulphide, about 0.2%, by volume, of carbon disulphide and about 0.1%, by volume, of N-methylaminoethanol, flows from the reflux condenser of the apparatus at normal pressure.

The yield of N-methyl-thiazolidine-2-thione, based on N-methylaminoethanol and on carbon disulphide, amounts to about 99.7%, including the losses owing to the waste gas.

EXAMPLE 2

The reaction apparatus consists of a 16-level bubble tray column. A condenser which is charged with cooling water is inserted between the first and second level. Moreover, the discharge from the 15th level communicates via a water-cooled condenser with the 16th level. One feed nozzle each is situated at the first level (A), 2nd level (B), 16th level (C) and at the sump outlet pipe (D). There are temperature measuring points at the first level ($T_1$), 5th level ($T_5$), 9th level ($T_9$), 14th level ($T_{14}$) and 16th level ($T_{16}$). The apparatus is continuously charged with the following quantities:

Nozzle A: 349 g/h of N-ethyl-aminoethanol
Nozzle D: 33 g/h of N-ethyl-aminoethanol
Nozzle B: 137 g/h of recirculation mixture
Nozzle C: 653 g/h of carbon disulphide.

The residence time of the liquid phase over all reaction zones is about 44 min.

The following temperatures are measured:

$T_1$ : 22° C.
$T_5$ : 147° C.
$T_9$ : 163° C.
$T_{14}$ : 171° C.
$T_{16}$ : 96° C.

630 g/h of pure N-ethyl-thiazolidine-2-thione are separated from the continuously issuing reaction mixture by distillation, while the remaining sump product is recirculated to the reservoir for the supply to nozzle B.

The N-ethyl-thiazolidine-2-thione, a brownish coloured oil, produced in this way has a melting point of from 10.8° to 11.1° C.

The yield is 99.8%, based on the amino ethanol used and the carbon disulphide.

EXAMPLE 3

Similarly to Example 1, 256 g/h of N-t-butylaminoethanol are reacted with 333 g/h of carbon disulphide to form 382 g/h of N-t-butylthiazolidine-2-thione having a melting point of from 69° to 70° C.

The reaction mixture contains only 2% of by-product once the carbon disulphide has been removed and may be used as a vulcanisation accelerator without separating the by-product by distillation.

EXAMPLE 4

The following quantities are continuously supplied to the apparatus described in Example 2 under a constant vacuum of 150 mbar:

Nozzle A: 700 g/h of N-cyclohexylaminopropanol-2
Nozzle D: 45 g/h of N-cyclohexylaminopropanol-2

Nozzle B: 630 g/h of recirculation mixture
Nozzle C: 794 g/h of carbon disulphide The residence time is 21 minutes.

1044 g/h of N-cyclohexyl-5-methyl-thiazolidine-2-thione having a melting point of from 86° to 88° C. are obtained.

We claim:

1. A process for the production of thiazolidine-2-thiones by the reaction of 1 mol of an amino ethanol with from 2 to 2.1 mol of carbon disulphide at from 20° to 200° C. and from 0.1 to 5 bar pressure, characterised in that the liquid phase containing amino ethanol is brought into intimate contact with the gaseous phase containing carbon disulphide in a continuous single stage process in at least two consecutive reaction zones, wherein the liquid phase is introduced continuously into the first reaction zone, conveyed toward the last reaction zone and removed downstream of the last reaction zone and wherein the gaseous phase is introduced continuously into the last reaction zone, conveyed toward the first reaction zone and removed downstream of the first reaction zone.

2. A process according to claim 1, characterised in that the total residence time of the liquid phase in the reaction zones is from 10 to 120 minutes.

3. A process according to claim 1, characterised in that the liquid phase is cooled upstream or downstream of the last reaction zone.

4. A process according to claim 1, characterised by removing a proportion of the reaction heat by evaporation of amino ethanol and thiazolidine-2-thione in the reaction zones.

5. A process according to claim 1, characterised in that the carbon disulphide still present in the liquid phase is removed downstream of the last reaction zone by the addition of amino ethanol.

6. A process according to claim 1, characterised in that the N-substituted thiazolidine-2-thione is separated from the liquid phase, removed and the remaining mixture of the by-products is recirculated into at least one reaction zone.

7. A process according to claim 1, characterised in that the by-product is fed to the amino ethanol flowing to the first reaction zone.

8. A process according to claim 1, characterised in that the gaseous phase is cooled upstream or downstream of the first reaction zone and the condensed liquid is supplied to at least one reaction zone.

* * * * *